(12) United States Patent
Fulton et al.

(10) Patent No.: US 11,406,516 B2
(45) Date of Patent: Aug. 9, 2022

(54) METHODS AND SYSTEMS FOR ANEURYSM STABILIZATION AND TREATMENT

(71) Applicant: Nfinium Vascular Technologies, LLC, Grand Junction, CO (US)

(72) Inventors: Richard Eustis Fulton, Grand Junction, CO (US); German Todorov, Atlanta, GA (US)

(73) Assignee: Nfinium Vascular Technologies, LLC, Grand Junction, CO (US)

( * ) Notice: Subject to any disclaimer, the term of this patent is extended or adjusted under 35 U.S.C. 154(b) by 108 days.

(21) Appl. No.: 16/121,274

(22) Filed: Sep. 4, 2018

(65) Prior Publication Data

US 2019/0070026 A1 Mar. 7, 2019

Related U.S. Application Data

(60) Provisional application No. 62/631,812, filed on Feb. 18, 2018, provisional application No. 62/578,484, filed on Oct. 29, 2017, provisional application No. 62/553,938, filed on Sep. 4, 2017.

(51) Int. Cl.

| | | |
|---|---|---|
| *A61F 2/86* | (2013.01) | |
| *A61F 2/07* | (2013.01) | |
| *A61F 2/95* | (2013.01) | |
| *A61F 2/82* | (2013.01) | |
| *A61B 8/12* | (2006.01) | |
| *A61F 2/06* | (2013.01) | |

(52) U.S. Cl.
CPC .................. *A61F 2/86* (2013.01); *A61F 2/07* (2013.01); *A61F 2/95* (2013.01); *A61B 8/12* (2013.01); *A61F 2002/068* (2013.01); *A61F 2002/077* (2013.01); *A61F 2002/823* (2013.01); *A61F 2002/9511* (2013.01); *A61F 2220/0008* (2013.01); *A61F 2250/0067* (2013.01)

(58) Field of Classification Search
CPC ................ A61F 2/945; A61F 2002/068; A61F 2002/077; A61F 2002/30583; A61F 2002/823; A61F 2/86; A61F 2/07; A61F 2/95; A61F 2250/0067; A61F 2002/9511; A61F 2220/0008; A61B 17/12118; A61B 8/12; A61M 2025/1052
USPC ....................................................... 623/1.31
See application file for complete search history.

(56) References Cited

U.S. PATENT DOCUMENTS

| | | | | |
|---|---|---|---|---|
| 5,578,071 | A | * 11/1996 | Parodi | ..................... A61F 2/954 623/1.19 |
| 5,683,449 | A | * 11/1997 | Marcade | ................... A61F 2/07 128/898 |
| 5,693,088 | A | * 12/1997 | Lazarus | ..................... A61F 2/07 606/195 |
| 7,252,834 | B2 | 8/2007 | Vyavahare et al. | |
| 8,679,057 | B2 | 3/2014 | Fulton, III et al. | |
| 8,740,961 | B2 | 6/2014 | Fulton, III | |
| 9,114,031 | B2 | 8/2015 | Fulton, III | |
| 9,126,016 | B2 | 9/2015 | Fulton, III | |
| 9,277,935 | B2 | 3/2016 | Fulton, III | |

(Continued)

*Primary Examiner* — Julian W Woo
(74) *Attorney, Agent, or Firm* — Sheridan Ross P.C.

(57) ABSTRACT

Devices and methods are described for delivering aneurysm stabilizing substances that may act in more than one pathway to the aneurysmal wall to prevent further enlargement of an aneurysm while allowing blood flow through the treatment area. Methods, devices and features for removal of the delivery device after the treatment are also disclosed.

9 Claims, 8 Drawing Sheets

(56) References Cited

U.S. PATENT DOCUMENTS

| | | | |
|---|---|---|---|
| 2006/0247760 A1* | 11/2006 | Ganesan | A61F 2/07 623/1.16 |
| 2006/0292206 A1* | 12/2006 | Kim | A61B 17/12186 424/443 |
| 2009/0005760 A1* | 1/2009 | Cartledge | A61F 2/954 604/534 |
| 2009/0210047 A1* | 8/2009 | Amplatz | A61F 2/07 623/1.12 |
| 2011/0282274 A1* | 11/2011 | Fulton, III | A61B 17/12168 604/28 |
| 2015/0343178 A1 | 12/2015 | Fulton, III | |

\* cited by examiner

METHODS AND SYSTEMS FOR ANEURYSM STABILIZATION AND TREATMENT

This U.S. Non-Provisional Patent Application claims the benefit of priority from U.S. Provisional Patent Application Ser. No. 62/553,938, filed Sep. 4, 2017, U.S. Provisional Patent Application Ser. No. 62/578,484, filed Oct. 29, 2017, and U.S. Provisional Patent Application Ser. No. 62/631,812, filed Feb. 18, 2018, the entire disclosures of which are hereby incorporated by reference in their entireties.

BACKGROUND

An aneurysm is a condition that occurs when part of an artery wall weakens, allowing the artery wall to "balloon" out or widen abnormally. Aneurysms can occur in any artery throughout a circulatory system, but the most common types of aneurysms are aortic aneurysms, cerebral aneurysms, popliteal artery aneurysms, mesenteric artery aneurysms, and splenic artery aneurysms. Aneurysms pose significant health risks, particularly in light of their ability to rupture. Embodiments of the present disclosure provide systems, methods, and devices that are suitable for use with various types of aneurysms and no limitation with respect thereto is provided herewith. Certain embodiments of the present disclosure are particularly well suited, however, with abdominal aortic aneurysms.

An abdominal aortic aneurysm ("AAA") is the expansion of the abdominal aorta beyond 3.0 cm in diameter. Such aneurysms may be identified through screenings or incidentally during an imaging study or CT scan that may be performed for another medical issue. However, the prior art provides no effective simple, minimally invasive treatment for AAAs and various other aneurysm conditions. When an aneurysm is discovered early on, patients must endure a "watch and wait" observation program until an aneurysm is enlarged enough to be suitable for surgery, which has been known to take years. Expansion of an aneurysm may justify a surgical procedure in the form of an open surgical repair or insertion of an endovascular stent graft. There is a litany of significant short term and long-term problems with both techniques that may be life threatening and need further adjunctive treatments. When the expansion of an aneurysm reaches approximately 5.0 cm in diameter, the risk of rupture begins to increase dramatically with elapsed time and further expansion of the aneurysm. This is the point at which the "watch and wait" strategy is abandoned because of the increased risk of rupture and surgical or endovascular correction of the issue is recommended.

Surgical repair of AAAs typically require a major abdominal operation with general anesthesia and an incision into the abdomen, dissection of the tissues, clamping of the aorta, incising the aorta, placing a tubular synthetic graft into the bed of the aorta, suturing the aorta in place, restoring flow, and closing the abdominal incision. The recovery period for such procedures may be significant. The mortality associated with the surgery is 5% at 30 days post surgery and 7% at 90 days post-surgery.

Endovascular repair is less invasive and with less perioperative mortality than surgery. At least one catheter is placed in one of the femoral arteries and guided by imaging techniques into the abdominal aortic aneurysm area and a tubular stent graft is deployed within the aneurysm under image guidance. The covered stent graft is expanded and secured into position and then the catheters removed. This technique avoids open surgery, but the procedure is complicated and dependent in part on the technical skill of the physician. Open surgery carries a greater operative risk immediately, but the lack of durability and the incidence of delayed complications such as endoleaks with endovascular repair cause the overall results of surgery versus endovascular repair to be essentially equal at eight years. Moreover, the repaired aorta must be followed closely after the intervention to detect complications and to evaluate the efficacy of the treatment. This follow-up must continue essentially for the life of the patient. Accordingly, there has been a long-felt and unmet need to provide a safer and more reliable treatment for aneurysm conditions, particularly AAAs and other small aneurysm conditions that were heretofore not suitable for surgery or other treatment.

U.S. Pat. No. 7,252,834 to Vyavahare et al., which is hereby incorporated by reference in its entirety, provides that application of certain phenolic substances to the wall of an aneurysm, such as an AAA will stabilize the elastin degradation process that contributes to the enlargement of the aneurysm.

The typical process of aneurysm formation and progression involves a gradual weakening and degradation of tissue matrix (primarily in the media and to a lesser degree the adventitia) that normally provides mechanical resilience to the aorta. This is caused by a complex interplay of interrelated factors that impact multiple processes, some or many of which may not be affected by the phenolic compounds in the prior art. Furthermore, there may be dominant pathways and adjunctive pathways, and the combination of different pathways may be different in different subjects, as well as different within the same subject at different times in the process of aneurysmal dilatation. The prior art addresses only one pathway. Even if the phenolic substances are effective at stabilizing elastin via the specific pathway affected by the phenolic substances, there are other pathways that result in aneurysmal enlargement that are not addressed by the prior art. Accordingly, a need exists for additional therapeutic approaches for treating aneurysms.

SUMMARY

Vyavahare discloses certain substances that may be useful in combination with devices of embodiments of the present disclosure. It should be recognized, however, that the present disclosure is not limited to use with any particular drug or substance and that other substances apart from those disclosed in Vyavahare, whether currently known or later developed or discovered, are contemplated as being provided in combination with devices of the present disclosure. Delivery devices of the present disclosure may be used with any number of substances to stabilize an aneurysm. Accordingly, the term "aneurysmal stabilizing substance" as used herein is not limited to any single or particular substance and refers to any substance that targets a biochemical pathway or mechanism affecting aneurysm formation and enlargement. One skilled in the art would understand that the examples of aneurysmal stabilizing substances provided herein are not intended to limit the scope of the invention. As used herein, the term "proximal" with respect to devices refers to the user-proximal end including, for example, an end of the device controlled by an operator. The term "distal," as used herein with respect to devices refers to a distal end of the device opposite the proximal end, and which is inserted into a patient. As used herein, the term "proximal" when used with respect to a patient generally means upstream in an artery, where "distal" refers to a downstream portion of an artery. The terms "cephalad," which refers to the head end of the patient or upper body, and "caudal," which refers to the lower body may also be used.

It is an object of the present disclosure to stabilize the growth of an aneurysm. Stabilization of aneurysm growth could potentially prevent thousands of major surgeries and endovascular repair procedures per year, obviate the costly and psychologically challenging follow up imaging studies to monitor the growth of the aneurysm and to evaluate for post-operative endoleaks and other complications. Stabilization of such conditions would save healthcare systems worldwide significant amounts of money and resources and provide a minimally invasive solution that is permanent.

It is an object of the present disclosure to provide substances, systems, methods and devices of delivering and applying one or more substances by one or more delivery methods to the tissues of the aortic wall to achieve one or more of stabilize, stimulate, or repair elastin, collagen, tissue matrix and other structures within the aortic wall to prevent or significantly slow the enlargement of the aorta. The substances, systems, methods and devices described herein overcome the limitations of the prior art of simplistic delivery devices and methods of a single substance or related substances that affect only one or limited pathways or modes action by providing means that address more than one pathway or related pathways and different delivery devices and methods.

Aneurysmal stabilizing substances or substances that may prevent or slow enlargement of arterial vessels by altering those pathways include, but are not limited to: (a) therapeutic agents inhibiting elastin, collagen and/or hyaluronan degradation and/or restoring or improving their production and deposition, including without limitation, tannins, polyphenols and related agents (epigallocatechin gallate (EGCG), white/green tea extract (high in EGCG), pentagalloyl glucose (PGG), tannic acid, grape seed extract, ruscogenins, *Ruscus aculeatus* extract (high in ruscogenins), diosmin, hesperidin, hederagenin, Escin, *Aesculus hippocastanum* extract (high in escin), pycnogenol, other elastase, collagenase or hyaluronidase inhibitors (doxycycline hyclate), inhibitors of cysteine proteinases (particularly inhibitors of cathepsins and calpain), inhibitors of serine proteinases (camostat), and enhancers of LOX/LOXL production and/or activity (dill seed extract); (b) therapeutic agents inhibiting/modulating inflammation in the aortic wall, including without limitation, lymphocyte function suppressors (cyclosporine), luekotriene receptor inhibitors, (montelukast, zafirlukast), nf-kb inhibitors, prostaglandin/leukotriene antagonists and synthesis inhibitors/modulators (COX, COX-2 enzyme inhibitors, omega-3 fatty acids DHA and EPA), immunomodulatory/anti-inflammatory cannabinoids (cannabidiol), Sphingosine-1-phosphate receptor modulators (fingolimod), agents that reduce free radical damage, such as antioxidants, free radical scavengers, oxidative stress modulators (superoxide dismutase, catalase, glutathione peroxidase, tocopherols, tocotrienols, glutathione), statins (atorvastatin, fluvastatin, lovastatin, pravastatin, rosuvastatin, simvastatin, pitavastatin), boosters of cellular NAD+ levels, (nicotinamide riboside (NR) and nicotinamide mononucleotide (NMN), and (c) therapeutic agents inhibiting apoptosis of cells in the aortic wall, including without limitation inhibitors of caspases (VX-765).

Aneurysmal stabilizing substances also include gene therapy agents that stimulate overexpression of genes encoding tissue inhibitors of matrix metalloproteinases (TIMPs), elastin, tropoelastin, transforming growth factor-beta1, LOX/LOXL, enzymes that reduce oxidative stress (superoxide dismutase, catalase, glutathione peroxidase), or that suppress expression of elastase, collagenase, hyualoronidase, cysteine proteinases, nf-kb, pro-inflammatory cytokines, caspases.

It is yet another object of the present disclosure to provide novel local and systemic delivery methods and systems that may be employed at the same or different times and settings, and that utilize two or more pathways of action to stabilize, repair and restore the aortic wall. For example, in some embodiments, a local delivery of a substance directly to the aortic wall is followed by oral, intravenous, and/or subcutaneous administration of certain adjunctive agents that act in different pathways of action and are mediated in different ways. The agents may be chosen from the agents that affect chosen pathways listed herein and may be administered by different routes and in different temporal sequences.

It is yet another object of the present disclosure to provide a solution to the delivery of an aneurysm stabilizing substance to the aneurysmal wall. The following U.S. Patents are hereby incorporated by reference in their entireties: U.S. Pat. No. 8,679,057 to Fulton, III et al., U.S. Pat. No. 8,740,961 to Fulton, III, U.S. Pat. No. 9,114,031 to Fulton, III, U.S. Pat. No. 9,126,016 to Fulton, and U.S. Pat. No. 9,277,935 to Fulton, III, all of which are incorporated herein by reference in their entireties.

In various embodiments of the present disclosure, methods, systems and devices are provided that enable safe delivery of an aneurysmal stabilizing substance to the aneurysm wall with as little outward radial pressure as possible. In some embodiments, adequate delivery of the aneurysm stabilizing substance to the aneurysm wall is provided by ensuring adequate contact of the substance containing membrane to the aneurysm wall. In some embodiments, devices and methods of the present disclosure provide "flow through" capabilities so that the blood flow in the aorta or other pathway is not occluded and the tissues and organs distally have an uninterrupted blood supply. Devices and systems of the present disclosure provide robust support to the device so that the pressures and blood flow in an artery does not significantly displace the device during deployment or during the subsequent substance transfer.

Embodiments of the present disclosure further provide systems, devices and methods for delivering a medicament or aneurysm stabilizing substance to tissues adjacent to the connective tissue for absorption into the connective tissue. In certain embodiments, non-phenolic compounds that may be combined with phenolic compounds and may affect one or more of elastin, collagen, and other tissues and may comprise anti-oxidant properties are delivered by devices and methods of this disclosure. Devices and systems of the present disclosure also provide synthetic compounds which have specific actions against MMP's, elastase, collagenase, and other proteinases.

Embodiments of the present disclosure are suitable for treatment of small, simple aneurysms that usually do not contain intraluminal thrombus and have a relatively low rupture risks, as well as larger aneurysms that may be irregular and contain moderate to large amount of intraluminal thrombus and possess a more significant rupture risk. Any feature or component of any one embodiment disclosed herein may be combined or substituted with any other feature or component of any other embodiment disclosed herein.

In some embodiments, aneurysm stabilizing substances are coated onto or applied to the covering of a stent like or a stent graft like structure on its abluminal side so that it may be transferred to an AAA wall. It is contemplated that substances, agents, methods, and systems described herein may be utilized with a conventional stent scaffold that is permanently implanted within the aorta.

In addressing simple aneurysms (e.g. 3.5-5.0 cm in diameter) with little or no thrombus, various embodiments are provided that comprise non-occlusive stent like devices that press the drug coated covering against the wall using a patient's own blood pressure. Such devices can be inserted and removed as shown and described herein.

In one embodiment, an intravascular device for treating an aneurysm is provided. The device comprises an expandable stent and an expandable membrane provided in communication with the expandable stent. At least one of the expandable stent and the expandable membrane is in communication with an insertion catheter. In various embodiments, insertion catheters and translatable insertion guide wires are contemplated as comprising those shown and described in U.S. Patent Application Publication No. 2015/0343178 to Fulton, III, which is hereby incorporated by reference in its entirety. Fulton, III shows, for example, an insertable device that can be actuated by a user to control and expand related features and devices (see FIG. 4B and related of Fulton, III) which is contemplated for use with at least some embodiments of the present disclosure. The expandable membrane and the expandable stent each comprise a distal end and a proximal end. The membrane comprises an inlet operable to receive blood flow at the distal end and an outlet operable to allow the egress of blood flow at the proximal end. The inlet comprises an area that is greater than an area of the outlet. The membrane is operable to be expanded at least in part by a force provided by a flow of blood entering the inlet, and the membrane comprises a flexible material that is operable to conform to an internal surface of an aneurysm for treatment thereof.

In one embodiment, a method of intravascular treatment of an aneurysm is provided. The method comprises providing a device comprising an expandable stent and an expandable membrane. At least one of the expandable stent and the expandable membrane is in communication with an insertion catheter. The membrane comprises an inlet operable to receive blood flow at a distal end thereof and an outlet operable to allow the egress of blood flow at a proximal end thereof. The inlet comprises an area that is greater than an area of the outlet. The device is inserted into an artery comprising an aneurysm and at least one of the membrane and the stent is expanded. Blood is allowed to flow unimpeded through at least one of the stent and the membrane for a predetermined amount of time as may be needed to apply a drug or otherwise treat the aneurysmal wall. The stent and/or membrane are then contracted, and the device is removed.

This Summary is neither intended or should it be construed as being representative of the full extent and scope of the present invention. The present invention is set forth in various levels of detail and the Summary as well as in the attached drawings and in the detailed description of the invention and no limitation as to the scope of the present invention is intended by either the inclusion or non-inclusion of elements, components, etc. in the Summary. Additional aspects of the present invention will become more readily apparent from the detailed description, particularly when taken together with the drawings.

BRIEF DESCRIPTION OF THE FIGURES

The accompanying drawings which are incorporated herein and constitute a part of the specification, illustrate various embodiments of numerous inventions and together with the general description of the invention given provide the detailed description, and the drawings serve to explain the principles of these embodiments.

It should be understood that the drawings are not necessarily to scale. In certain instances, details that are not necessary for an understanding of the invention or that render other details difficult to perceive may have been omitted. It should be understood, of course, that the invention is not necessarily limited to the particular embodiments illustrated herein.

DETAILED DESCRIPTION

Figure 1:
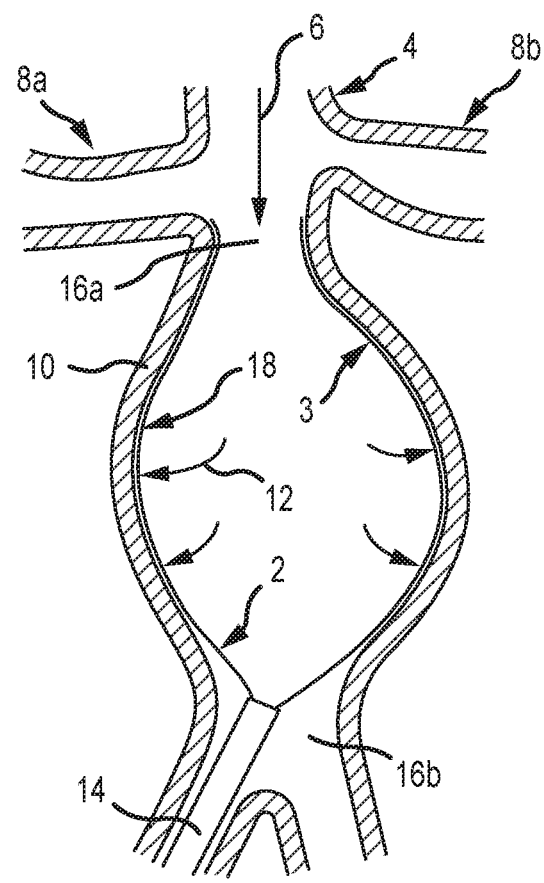
FIG. 1 is a cross-sectional view of a device of the present disclosure provided within an artery.

FIG. 1 depicts an aneurysm stabilizing substance delivery device 2 according to one embodiment of the present disclosure. The device 2 is provided within an artery 4. In the depicted embodiment, the artery 4 comprises an abdominal aortic aneurysm ("AAA"). Embodiments of the present disclosure are particularly well suited for treating aneurysms in the AAA which commonly occur below the renal arteries. It should be recognized, however, that the location of deployment and use of devices according to the present disclosure are not limiting and devices, systems and methods provided herein may be employed in various intravascular locations throughout the anatomy of humans and other animals. As shown in FIG. 1, the artery 4 comprises a blood flow 6 therethrough and an AAA 10 depicted as an expanded portion of the artery 4 below the renal arteries 8a, 8b. A blood pressure 12 is depicted as a radially outward force on the device 2 and the artery 4 of FIG. 1.

The device 2 of FIG. 1 comprises a covered stent-like structure, which may be self expandable, with a relatively high hoop strength at first and second ends of the device to anchor the device 2 to the respective aneurysm necks 16a, 16b. A middle or "belly" portion 18 of the device 2 comprises a low hoop strength. The belly portion 18 comprises sufficient hoop strength and longitudinal strength for deployment and recovery into and out of the delivery sheath 14. The belly portion 18, however, is also flexible enough to contact an aneurysm wall without much lateral radial force.

In the embodiment of FIG. 1, the stent-like structure of the device 2 is comprised of anchoring sections at or proximal to first and second ends 16a, 16b of the device 2. The proximal and distal ends 16a, 16b comprise areas of enhanced hoop strength and a flexible section of lower hoop strength provided between the first and second ends. In some embodiments, an impermeable elastomer or other material covers the stent-like structure, preferably on its abluminal side. In further embodiments, an impermeable elastomer is attached to or made part of the stent like structure and may cover all of it or only part of it. This configuration, shown in FIG. 1, allows the expansion of a substance-containing portion of the device 2 to contact the AAA wall, in part due to a force provided by the patient's blood pressure 12, with assistance from an inherent outward radial force of the stent like structure.

Figure 2:
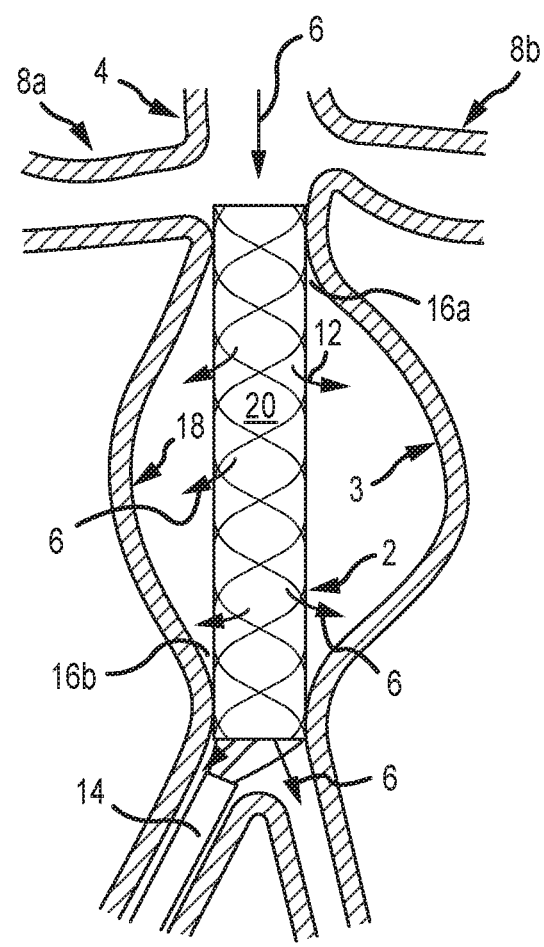
FIG. 2 is a cross-sectional view of a device of the present disclosure provided within an artery.

FIG. 2 depicts an aneurysm stabilizing substance delivery device 2 according to another embodiment of the present disclosure. The device 2 of FIG. 2 is provided within an artery 4 and in a similar position relative to the artery as the device of FIG. 1. The structure of the aortic artery and related description from FIG. 1 is hereby incorporated by reference.

FIG. 2 depicts a device 2 with internal stent structure 20 to provide enhanced structural support to the device 2. The stent 20 is not attached to the belly portion 18 of the device 2, which preferably comprises a drug-coated mid-portion. The stent 20 of FIG. 2 is attached to the remainder of the device 2 at proximal and distal ends 16a, 16b. The stent 20 provides structural support and stability to the device 2 for accurate placement and positioning thereof while a covering or membrane of the belly portion 18 comprises a stabilizing substance that is generally free to approximate and contact the vessel wall 10. A patient's blood pressure 12 expands the drug coated membrane to the vessel wall 10. Alternatively, a means to assist the expansion of the drug coated membrane may also be provided. For example, in some embodiments, a soft, compliant balloon catheter is provided within or interior to the membrane and is capable or providing an outward force to the membrane. An external force provided by a patient's blood pressure, for example, is operable to expand the balloon and membrane outwardly toward the aneurysm wall. It is also contemplated that guide wires, non-balloon catheters, and/or balloon catheters are provided to interstices in a stent.

In some embodiments, an elongated guide wire type device is inserted through the stent interstices and fed into the space between the stent and the membrane. The device is preferably removed after a prolonged contact of the membrane and the aortic wall. Continued insertion will result in coiling and accumulation of the guide wire type device which will compress the membrane outward to contact the aneurysmal wall. Hence, space occupying means may be inserted into this space to compress the membrane against the aortic wall in the case the membrane is not completely approximated to the aneurysm wall by the patient's blood pressure.

In some embodiments, the membrane and/or belly portion 18 may be folded over distal ends of the stent 20 for insertion through an outer delivery sheath 14. The stent 20 preferably comprises points of attachment to the belly portion 18 of the device 2 at first and second ends 18a, 18b of the device. The membrane or belly portion 18 is expandable and not attached to a central portion of the stent 20, thereby allowing the belly portion 18 to expand outwardly and be compressed against the interior of the AAA by the blood pressure within the aneurysm. The belly portion 18 and associated coating, substance, or drug on the abluminal surface is thus operable to contact the walls of the AAA.

In various embodiments, methods treating an aneurysm are provided. In some embodiments, methods comprise providing a device 2 as shown in FIG. 2. The stent 20 and drug-coated membrane are inserted into an intravascular space, and at least a portion of the device is expanded. Preferably, one end of the stent is anchored in the immediate infrarenal aorta, allowing the membrane to expand against the aneurysmal wall. A period of time is allowed to elapse for a drug or substance to transfer from the device to the wall of the associated blood vessel. Subsequently, the stent and/or membrane are collapsed and removed. In some embodiments, a stent 20 is provided as a structural device to aid insertion and expansion of the membrane 18. In such embodiments, the stent 20 is selectively expanded to place the membrane in contact with an aortic wall (for example) and subsequently retracted so that blood flow is not directed through the stent, but rather flows exterior to the stent to contact the aortic wall and subsequently to pass through to other regions of a vascular system and body via the outlet of the device 16b.

Figure 3:
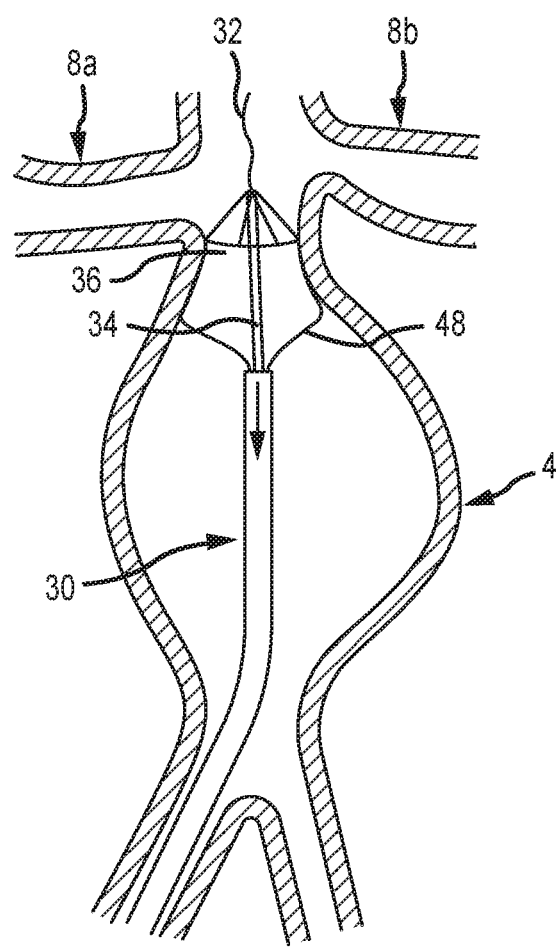
FIG. 3 is a cross-sectional view of a device of the present disclosure provided within an artery.

FIG. 3 depicts an aneurysm stabilizing substance delivery device 30 according to yet another embodiment of the present disclosure. The device 30 of FIG. 3 is shown as being provided in an aortic aneurysm 4. As previously stated, however, devices of the present disclosure are not limited to use with or within an aortic artery or AAA. The device 30 comprises a flexible guide wire 32. The flexible guide wire 32 is provided coaxially within a tubular member 34 to stabilize a distal attachment portion 36 of the device 30 and prevent distal migration of the device 30 due to aortic pressure. It is known that the aorta comprises a significant volume of blood flow and pressure. It is an object of various embodiments of the present disclosure to provide an expandable drug or substance delivery device that is operable to be secured in an intended location and that prevents unintended movement and dislocation due to blood flow and blood pressure. FIG. 3 illustrates one embodiment wherein a relatively rigid tube 34 is provided. The tube 34 is selectively attached to a distal end 36 of the device(s) 30 to stabilize the device for one or more of deployment, placement, delivery of substance, and subsequent removal. A guide sheath or catheter 36 is provided for insertion and extraction of the device 30.

Figure 4:
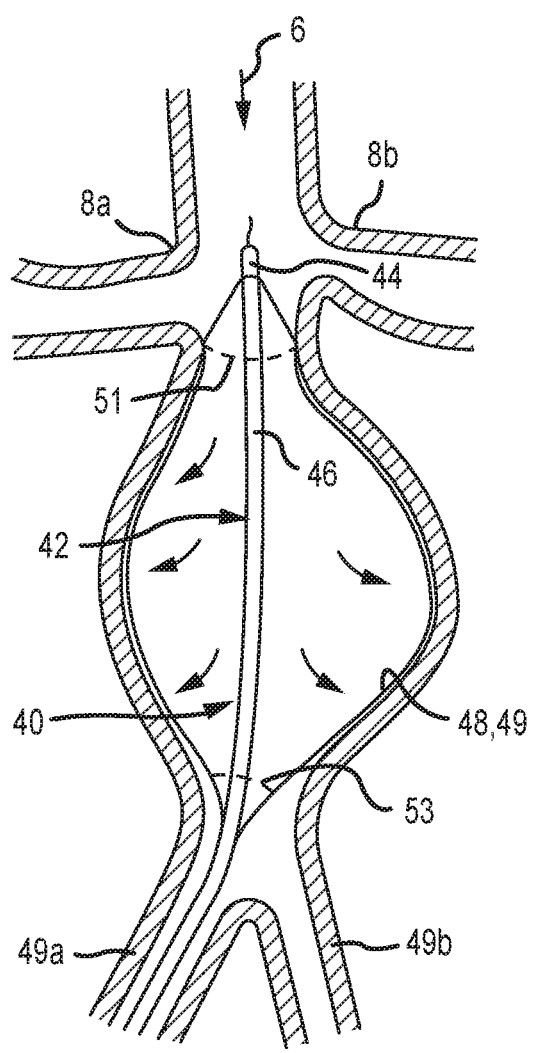
FIG. 4 is a cross-sectional view of a device of the present disclosure provided within an artery.

In the embodiment of FIGS. 3-4, an expandable braid, scaffold, or stent is attached at the respective ends of an inner and outer tubular member. The distal or cephalic portion of the stent 48 has a high hoop strength scaffolding to anchor the device in the infrarenal area (which is usually not dilated) and the portion between the distal and proximal sections comprises a flexible stent like scaffold that is operable to conform to the inside of the aneurysm thereby compressing the membrane against the aneurysmal wall. The proximal or caudal attachment segment may also have a higher hoop strength than the belly for attachment purposes.

The device shown in FIGS. 3-4 is operable for use in an aorta, and/or to deliver a substance to other arteries by providing a flow through channel. The device 40 of FIG. 4 comprises a catheter 42 with coaxial inner 44 and outer 46 members. The catheter 42 is preferably provided as a component of an intravascular device 40. A stent portion 48 is provided that comprises a braid or other scaffold configuration. The distal end of the stent 48 is attached to the distal end of the inner member and the proximal end of the stent like device may be attached to the outer member.

The inner 44 and outer 46 members of the catheter 42 are preferably translatable relative to one another. By withdrawing the inner member 44 relative to the outer member 46, the stent 48 is compressed and expands outwardly. By advancing the inner member 44 relative to the outer member 46, the expandable stent 48 will elongate and collapse over the inner member for insertion and withdrawal or removal. This simple push-pull mechanism allows for easy expansile deployment and easy collapsibility for removal. In some embodiments, the expandable stent 48 of FIG. 4 comprises a covering or membrane 50 which comprises an elastomer, fabric, or other substance or combination thereof which may be elastomeric. The membrane 50 is preferably impermeable to blood and fluids, but may be partially permeable or permeable to blood and fluids.

In some embodiments, the membrane 50 is impervious to liquids and is coated with or comprises an aneurysm stabilizing substance including, for example, a substance selected from any one of the following: (a) therapeutic agents inhibiting elastin, collagen and/or hyaluronan degradation and/or restoring or improving their production and deposition, including without limitation, tannins, polyphenols and related agents (epigallocatechin gallate (EGCG) white/green tea extract (high in EGCG), pentagalloyl glucose (PGG), tannic acid, grape seed extract, ruscogenins, *Ruscus aculeatus* extract (high in ruscogenins), diosmin, hesperidin, hederagenin, Escin, *Aesculus hippocastanum* extract (high in escin), pycnogenol), other elastase, collagenase or hyaluronidase inhibitors (doxycycline hyclate), inhibitors of cysteine proteinases (particularly inhibitors of cathepsins and calpain), inhibitors of serine proteinases (camostat), and enhancers of LOX/LOXL production and/or activity (dill seed extract); (b) therapeutic agents inhibiting/modulating inflammation in the aortic wall, including without limitation, lymphocyte function suppressors (cyclosporine), luekotriene receptor inhibitors, (montelukast, zafirlukast), nf-kb inhibitors, prostaglandin/leukotriene antagonists and synthesis inhibitors/modulators (COX, COX-2 enzyme inhibitors, omega-3 fatty acids DHA and EPA), immunomodulatory/anti-inflammatory cannabinoids (cannabidiol), Sphingosine-1-phosphate receptor modulators (fingolimod), agents that reduce free radical damage, such as antioxidants, free radical scavengers, oxidative stress modulators (superoxide dismutase, catalase, glutathione peroxidase, tocopherols, tocotrienols, glutathione), statins (atorvastatin, fluvastatin, lovastatin, pravastatin, rosuvastatin, simvastatin, pitavastatin), boosters of cellular NAD+ levels, (nicotinamide riboside (NR) and nicotinamide mononucleotide (NMN), and (c) therapeutic agents inhibiting apoptosis of cells in the aortic wall, including without limitation inhibitors of caspases (VX-765). The coating is preferably provided on the abluminal side of the membrane 50. The expandable stent 48 is constructed so as to exert very little outward radial force. In some embodiments, the stent comprises small and/or flexible fibers to maintain a cylindrical shape while exerting minimal outward radial force.

It is an object of the present disclosure to provide a device and system that causes contact of an aneurysm-stabilizing-substance-containing-membrane with an aortic wall while adding limited additional outward radial pressure, and to maintain the transmission of normal physiologic systolic and diastolic pulse pressures to the wall. The minimal outward radial force generated by the aneurysm substance delivery devices described herein will be less than 10%, and preferably less than 1%, of the outward radial force generated by the patient's own blood pressure. Hence, in this configuration the added radial force to effect contact of the aneurysm stabilizing substance bearing membrane on the weakened and compromised aortic wall will be minimal. The outward radial force of the device may be limited to an amount that causes it to expand outward but less than the amount needed to effect uniform contact with the aortic wall, as the patient's blood pressure will expand the membrane component in many embodiments to the aortic wall and hold it in place to deliver the aneurysm stabilizing substance to the wall. The current invention also will transmit the normal physiological systolic and diastolic pressures within the aorta to the aortic wall where physiologic processes within the aortic wall are at least partially dependent upon the normal physiological pulses to function properly. An inflated balloon, for example, only transmits more radial pressure to the weakened wall, and would also prevents the physiologic transmission of the systolic and diastolic pressures which may further weaken the aortic wall. The designs and embodiments contained herein solve both of these problems that may occur with balloon delivery devices, and they obviate the problems that other delivery devices may cause.

Ignoring the size of a vessel for convenience purposes, and only for example, if one were to occlude a blood vessel in a patient with a systolic blood pressure of 150 mm Hg, the balloon would have to achieve 285 grams of outward radial pressure to equal the same pressure as the transmitted systolic blood pressure. To overcome the systolic blood pressure and compress the balloon against the aortic wall, the balloon pressure must be greater than 285 grams. Hence, the balloon will be overinflated to insure good contact of the substance containing balloon surface with the weakened aortic wall and likely will generate 350 grams of outward radial force while not transmitting the physiological pulsations. This may be enough to damage the vessel wall, further weaken it, and predispose to rupture immediately, subacutely, or even a delayed rupture that may occur months later. In certain preferred embodiments, devices, systems and methods of the present disclosure provide less than 30 grams of outward radial pressure and some provide less than 10 grams of outward radial pressure to effectively expand the membrane component allowing the patient's blood pressure to provide the vast majority of the outward radial pressure (>90%) needed to approximate the membrane component to the aortic wall for efficient transfer of the aneurysmal stabilizing substance. Hence, the present disclosure provides safer solutions over alternative methods of delivering substances to the aortic wall by exerting a minimal amount of outward radial pressure which is insufficient to damage the aortic wall.

The expandable stent 48 and associated membrane 49 may cover more of the structure 40 at its flow outlet end than at its flow entrance end. The flow outlet end or the outlet aperture may be smaller than the inlet end or the inlet aperture. This results in a flow entrance aperture that is larger than the outlet flow aperture of the device, thereby causing a relative restriction of flow within and through the device 40. The restriction of flow may cause the membrane 49 to expand and approximate the wall of an AAA by the blood pressure within the device 40 and maintain the membrane 49 against the AAA wall during a substance delivery phase. Preferably, a patient's blood pressure expands the membrane 49 against the wall of the AAA, and little added radial pressure is required from the device 40.

At times, there may be reverse collateral flow from one of the lumbar arteries or the inferior mesenteric artery (IMA) that normally branch from the aorta into the space or potential space between the abluminal surface of the device membrane 49, which is coated with the stabilizing substance, and the aortic wall. This flow will likely have a systolic pressure lower than the systolic pressure within the aortic aneurysm, which would prevent less then optimal contact of the member and the aortic wall if the systolic and diastolic phases were synchronized. However, because of the circuitous route the collateral flow must take to arrive at the orifice of the lumbar or inferior mesenteric arteries, the systolic pressure within the aneurysm may be out of phase with the systolic pressure in the lumbar vessel or IMA. To prevent retrograde flow in the lumbar arteries and/or IMA at all times in the blood pressure cycle and to prevent displacement of the stabilizing substance containing membrane 49 from being displaced away from the aortic wall by this retrograde blood flow, the diastolic pressure within the AAA must exceed the systolic pressure within the lumbar arteries and/or IMA. Hence, in any of the embodiments herein, a means may be provided that would narrow the flow through feature outlet or proximal end of the device. In some embodiments, this means comprises an annular collar or ring at the distal end or outlet of the device to provide a maximum outlet diameter of the device 40 and thereby provide a constriction over the length of the device 40 at least when the device is expanded (see FIG. 1, for example). This restriction of flow may increase the diastolic pressure within the AAA so that the diastolic pressure within the AAA remains greater than the systolic pressure in the lumbar arteries and/or IMA. Hence, this embodiment configuration solves the problem of collateral flow displacing the membrane from the aortic wall.

The means that restricts the flow comprise one of several different configurations including, but not limited to, narrowing the outlet by fixed or adjustable means. Preprocedural measurements of the dimensions of the inlet and outlet and other parameters of the aneurysm may be made from imaging studies such as CT scans or MRI's that allow the practitioner to choose a device of the correct sizes that are specific to the patient's anatomy. Hence, the outlet size and the inlet size may be chosen before the procedure in the majority of cases. These flow restricting means may include a collar around the caudal aspect of the delivery device in which the internal dimension is smaller than the cephalic end of the delivery device. If there is a need to adjust the size of the outlet during the procedure, the collar may be expandable by a balloon. An additional catheter with an expandable member may be inserted into the outlet to create a smaller lumen and more resistance to the outflow which also would increase the diastolic pressure within in the device and the aneurysm. Alternatively, a toroidal like balloon or other balloon configuration may be provided about the outlet aperture. Inflating the balloon will constrict the caudal outlet aperture so that less blood will flow through the outlet aperture, thereby increasing the mean arterial pressure within the aorta proximally.

If adjustable means are utilized, means may be present for the operator to control the flow from the outlet of the device to keep the diastolic pressure elevated so that the membrane makes consistent and continued contact with the AAA wall. Pressure measuring means may also be present that detects, transmits, and/or monitors pressures within the device. These means may be connected and/or integrated with systemic and other measurements to alert the user of the diastolic pressures within the AAA treatment device relative to systemic and other measurements. For example, if a certain percentage of the systolic systemic pressure comes close to exceeding the AAA diastolic pressure (and, hence, the possibility exists that there retrograde flow may occur through the lumbar arteries and/or IMA which may prevent proper approximation of the membrane to the aortic wall), the user may adjust the means at the outlet region of the device to narrow the outlet and increase the diastolic pressure within the aorta to a level safely above the calculated systolic pressure in the lumbar arteries and/or IMA.

The pressure readings in the lumbar arteries and/or IMA can be determined during the procedure prior to deployment of the delivery device by inserting the end of a standard catheter into the orifice of the lumbar artery or arteries/IMA and taking pressure readings. Then pressures can be taken in the AAA and these pressure readings compared as to AAA diastolic vs. lumbar/IMA systolic to determine if there should be any concern or not. Decisions can then be made to choose a device with a narrowing means near the outlet or not.

Alternatively, if the lumbar/IMA systolic pressures are close to the diastolic pressure of the AAA, the lumbar/IMA may be embolized prior to the delivery device being inserted or deployed. Further, preoperative CTA or other imaging means may document lumbar arteries of a sufficient size that may warrant prospective embolization and occlusion. This would serve two purposes: 1) it would occlude the artery and prevent reverse flow that may displace the substance containing membrane away from the aneurysmal wall, and 2) it would diminish and reverse flow in the other lumbar arteries as they would have to collateralize the runoff of the occluded artery. Hence, occluding one or two arteries may diminish all reverse collateral flow.

Another method and means of insuring wall contact of the membrane is to assess the deployment of any of the proposed embodiments with intravascular ultrasound (IVUS) after deployment of the delivery device during the procedure. IVUS has the ability to confirm proper membrane apposition with the AAA wall and detect areas in which there may be less than optimal or no apposition and this can be done during the procedure. In some embodiments, analysis using IVUS occurs after the device is deployed and if areas of less than optimal membrane approximation are found, then and adjunctive device or means is inserted to compress the membrane against the AAA wall. In various embodiments, this compression is achieved by the use of a removeable stent like structure, catheter, and/or guide wire to compress the luminal surface so that the abluminal surface of the delivery device membrane is compressed against the arterial wall. The success of this device and operation is monitored or assessed by IVUS and adjustments can be made in real time. All of the interrogating may be performed with IVUS or any other imaging or assessment tool.

The device of FIG. 4 comprises areas that are devoid of a membrane 49 near the proximal and distal ends of the device 40 to allow blood to flow therethrough. The areas devoid of a membrane 49 generally comprise the ends of the stent 48 where the stent attaches to the inner and outer members 44, 46. The device 40 comprises a flow outlet aperture with a diameter that is less than a diameter of the flow entrance aperture. While the size of the inlet and outlet of the device will vary because of the specific patient's anatomy, the size of the inlet aperture will be at least 20% greater than the size of the outlet aperture. These measurements may range from and inlet aperture diameter of 2.5-6.0 cm and an outlet aperture diameter of 2.0 to 5.0 cm. This tapered or constricted arrangement with the outlet aperture smaller than the inlet aperture will cause the inner surface of the membrane 50 and/or stent 48 to balloon out in a funneled or tapered manner. The blood pressure within the device 40 thus presses the inner or luminal surface into the aortic wall. (See FIGS. 2 and 4, for example). This pressure against the wall with this configuration and method is essentially the same existing pre-procedure baseline pressure on the aortic wall which limits the potential of rupture. The membrane 49 in various embodiments comprises an expandable elastomer, such as silicone. In some of the embodiments, silicone may be inappropriate, and various other material suitable for the application as will be recognized by one of ordinary skill in the art are provided in or as the membrane 49. The membrane may be permeable, semi-permeable, or impermeable to blood.

Figure 5:
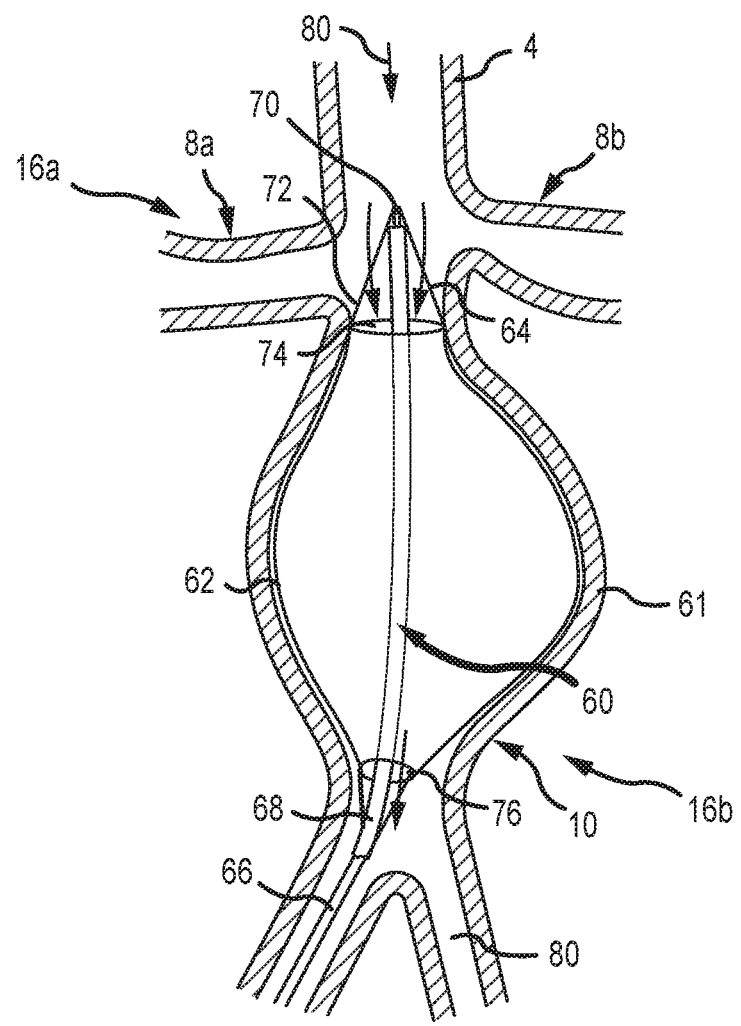
FIG. 5 is a cross-sectional view of a device of the present disclosure provided within an artery.

FIG. 5 depicts an aneurysm treatment device 60 according to one embodiment of the present disclosure. As shown, the device 60 comprises an expandable membrane 62 provided on an expandable stent 64. The stent 64 is in communication with elongate first and second members which comprise an inner member 66 and an outer member 68. The inner and outer members 66, 68 preferably comprise rigid or substantially rigid members capable of withstanding a compressive force to enable insertion of the device into an artery. The stent or scaffold 64 and membrane 62 are connected at their proximal and distal ends to the insertion members 66, 68. In the depicted embodiment, the membrane 62 and stent 64 are connected to the insertion members 66, 68 by substantially rigid guide wires 72. A distal end 70 of the device is inserted to a point preferably upstream of the renal arteries 8a, 8b of a patient. A blood flow 80 is provided and generally comprises a top-to-bottom flow in FIG. 5.

In the embodiment of FIG. 5, the depicted artery comprises an aneurysm 61 requiring treatment. The device 60 is operable to treat the aneurysm 61 by inserting the inner member 66, the outer member 68, the membrane 62 and the stent 64 into an internal volume of the aneurysm. The initially-contracted stent and membrane are expanded to the position shown in FIG. 5 by translating the inner member 66 relative to the outer member 68. Specifically, the inner member is extracted or translated caudally (i.e. downwardly in FIG. 5) to provide a compressive force to the guide wires 72, the membrane 62 and the stent 64. The compressive force at least partially expands the stent and membrane toward the aneurysm.

As further shown in FIG. 5, a distal or upstream end of the membrane 62 and the stent 64 comprises an inlet 74. The proximal or downstream end of the membrane 62 and the stent 64 comprises an outlet 76. In the depicted embodiment, the inlet 74 comprises a greater area than an area of the outlet 76. This discrepancy provides for a build-up of pressure within the membrane and stent, wherein a mass-flow rate of blood 80 into the device is slightly greater than a mass-flow rate of blood out of the device. The resulting pressure increase expands the membrane 62 and stent 64 to contact and contour to the aneurysm.

For illustrative purposes, an exterior portion 68 of the insertion catheter is only partially shown. As will be recognized by one of ordinary skill in the art, the insertion catheter, including inner 66 and outer 68 portions thereof, extend outside of a surgical workspace such that proximal ends of the catheter (not shown in FIG. 6) are accessible to a user or surgeon.

In various embodiments, including that shown in FIG. 5, the membrane 62 comprises at least one of a drug, compound, and a substance for treating an aneurysm. The contact of the membrane 62 with the artery wall as shown in FIG. 5 thus places a medicament, drug or substance in direct contact with an aneurysm.

In one embodiment, a method of use of the device of FIG. 5 is provided for treating aneurysms. The method comprises selecting an aneurysm to be treated; inserting and deploying a stent with a membrane within an artery; the membrane comprising an aneurysm stabilizing substance; wherein the deploying step comprises a push-pull motion of an inner and outer coaxial member; allowing a predetermined period of time to elapse with the stent and/or membrane expanded to allow for the aneurysm stabilizing substance to be transferred to an artery wall; collapsing the stent and/or membrane; and removing the device from the artery.

Another embodiment may target larger and more complex aneurysms with one or more of significant thrombus burden, tortuosity, elongation, kinking, irregular neck which makes sealing difficult, and/or saccules. All or some may be present in one aneurysm which makes delivery of any aneurysm stabilizing substance difficult if a membrane were to be used, as the profound irregularity of the wall in these complex aneurysms would make adequate apposition of the membrane unlikely in some areas. Moreover, these complex aneurysms not only tend to be larger and irregular, but 80% of them contain intraluminal thrombus of varying thicknesses. This thrombus, which lines the walls and may be fairly extensive would present a barrier to the transfer of the aneurysm stabilizing substance to the vessel wall, and potentially prevent adequate substance from reaching the wall. These complex aneurysms can likely best be treated using a liquid infusion rather than a drug or substance-coated membrane to permeate the clot better and to coat all the nooks and crannies of the complex aneurysm. Accordingly, various embodiments of the present disclosure comprise a non-occlusive device to deliver a liquid stabilizing substance to the aneurysm wall and recover at least most of it after a certain period of time.

Figure 6:
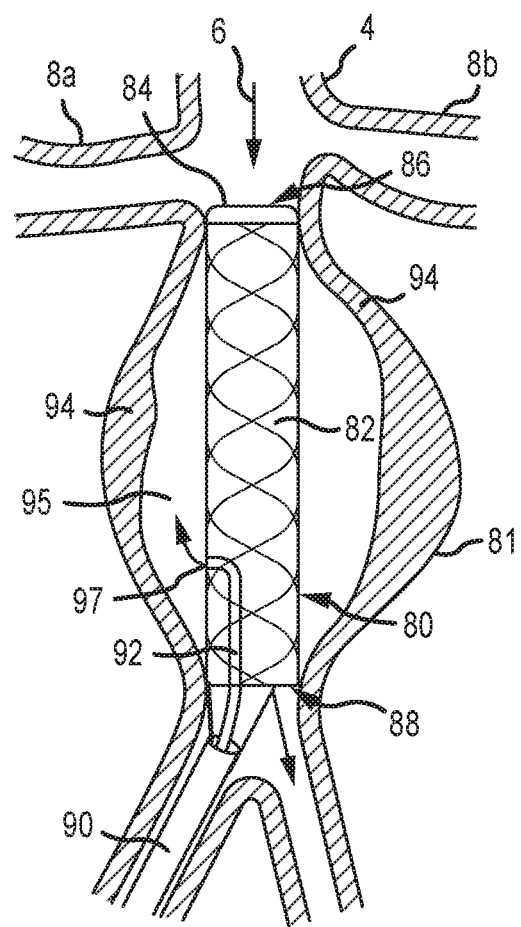
FIG. 6 is a cross-sectional view of a device of the present disclosure provided within an artery.

FIG. 6 demonstrates an example of a liquid drug delivery embodiment of the current invention and is a cross-sectional view of an aneurysm treatment device 80 according to another embodiment of the present disclosure. The device 80 of FIG. 6 comprises a covered stent 82 that is operable to provide a conduit to maintain blood flow through an artery during treatment of an aneurysm, and to exclude the aneurysm channel from blood flow 6. The stent 82 is impermeable to blood or fluids. The stent 82 comprises a securing means in the form of a selectively expandable toroidal balloon 84 at a distal end 86 of the device, and wherein the toroidal balloon 84 is operable to contact an interior wall of an aorta caudal to the renal arteries 8a, 8b and channel blood flow 6 through the stent 82 to an outlet 88 provided downstream of the affected area of the aneurysm.

The device 80 of FIG. 6 further comprises a drug delivery conduit 92 extending through or proximal to an insertion catheter 90 of the device 80. The drug delivery conduit 92 comprises an outlet 97 for delivering a drug or substance to an interior volume of an aneurysm external to the covered stent 82. The drug or substance is preferably operable to treat an aneurysm and, in some embodiments, comprises an agent that promotes formation of a clot 94 as a means to remedy the aneurysm.

The device 80 of FIG. 6 may comprise various entry and exit conduits even though a single conduit 92 is shown. In some embodiments, the device 80 comprises various collection and injection apertures that fluidly connect to an aneurysm sac. After deployment of the device 80 as shown, the blood within the sac may be aspirated or flushed through the conduit 92 and the fluid aneurysm stabilizing substance may be injected into the sac, essentially bathing the aneurysmal wall with the fluid aneurysm stabilizing substance. Only one aspiration/injection port is illustrated 92, but additional conduits are contemplated. In some embodiments, the device 80 comprises dedicated conduits for aspiration and injection, respectively.

The means by which the sac 95 is aspirated and substance is injected may be a part of the device as shown in FIG. 6 or it may be an integral part of the device or may be separate and inserted before or after the device is deployed and the sac is excluded. One method of the present disclosure contemplates inserting the aspiration/injection catheter(s) prior to the deployment of the stent, and deployment of the stent then occurs over the aspiration/injection catheter(s) leaving the aspiration catheter shaft pinned between the expanded stent and the aortic wall. Alternatively, an impermeable covering of the stent 82 like structure may be punctured by a device to deliver a substance to the sac 95.

Figure 7:
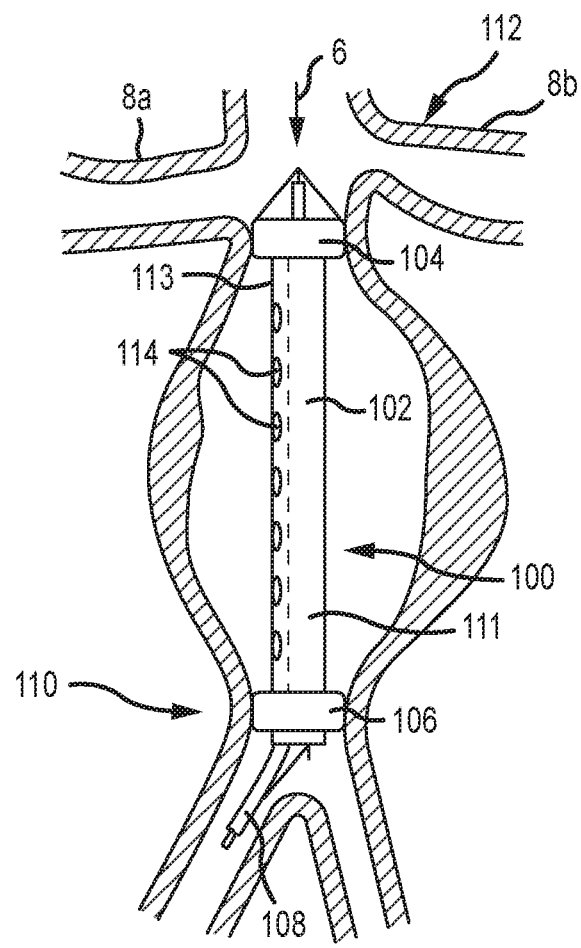
FIG. 7 is a cross-sectional view of a device of the present disclosure provided within an artery.

FIG. 7 depicts an aneurysm treatment device 100 according to another embodiment of the present disclosure. As shown, the device 100 is inserted into an aneurysm. The device comprises an expandable section 102 between first and second toroidal balloon members 104, 106. An insertion member 108 is provided that generally comprises an insertion catheter with translatable inner and outer members similar to those shown and described with respect to FIG. 5.

The expandable section 102 of the embodiment of FIG. 7 is subdivided into two sections comprising a blood flow channel 111 and a treatment channel 113. At least when the first toroidal balloon 104 is expanded, a patient's blood flow is confined to and channeled through the blood flow channel 111. The treatment channel 113 is preferably not in fluid communication with the blood flow channel 111 and comprises a means to irrigate, aspirate, and drain blood from the aneurysm. The treatment channel 113 is further operable to deliver drugs or other substances to the wall of an aneurysm.

As shown in FIG. 7, a cephalic toroidal balloon 104 is expanded in the immediate infrarenal artery 112 and a second caudal toroidal balloon 106 is expanded in the distal abdominal aorta 110. The blood flow channel 111 is comprised of a stent-like structure or other material and can be expanded by a push-pull action of an inner and outer members as described herein. The blood flow channel can also be at least partially expanded by the inflation of the two balloons 104, 106. The treatment channel 113 comprises a plurality of lumens 114 to enable the insertion and removal of materials, fluids, etc. from the aneurysmal sac.

In various embodiments, methods of use of the device 100 of FIG. 7 are provided. In one embodiment, the method comprises placing the device 100 within an aorta, expanding the blood flow channel 111, inflating the balloons 104, 106, flushing or irrigating the blood in the excluded aneurysmal sac via the treatment channel 113, injecting a fluid aneurysm stabilizing substance through the treatment channel 113, waiting a period of time, and flushing and/or irrigating the excluded aneurysmal sac to remove most of the substance and then removing the device. Methods of use for different embodiments of the present disclosure are similar for the those targeting small, uncomplex aneurysms and for those targeting larger, complex aneurysms.

In the embodiment of FIG. 7, the first and second expandable portions 104, 106 are contemplated as comprising balloons that are selectively inflatable and collapsible via air pressure. In some embodiments, a conduit for conveying pressure and air to the expandable portions is incorporated with the insertion catheter 108. Additionally, guide wires are preferably provided at a proximal end of the device, as well as the distal end of the device 100. The guide wires of the proximal end of the device are operable to be provided in tension to withdraw or extract the device, and guide wires of the distal end of the device are operable to be provided in tension during insertion of the device.

As previously stated, the insertion catheter of various embodiments of the present disclosure, including FIG. 7, is contemplated as comprising features and devices disclosed in U.S. Patent Application Publication No. 2015/0343178 to Fulton, III, which is hereby incorporated by reference in its entirety.

Figure 8:
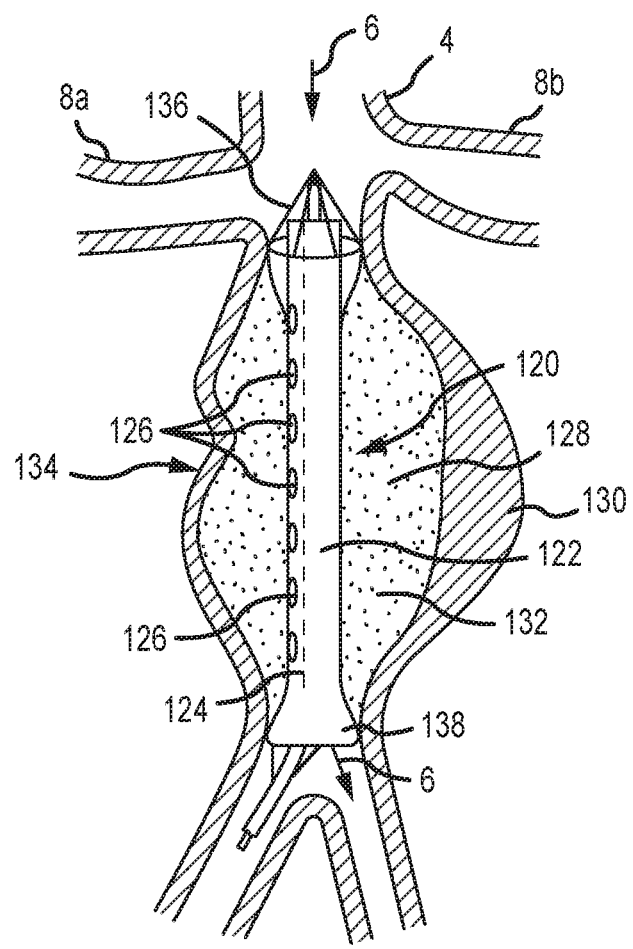
FIG. 8 is a cross-sectional view of a device of the present disclosure provided within an artery.

FIG. 8 depicts an aneurysm treatment device 120 according to yet another embodiment of the present disclosure. As shown, the device 120 comprises a central portion comprising a blood flow channel 122 and a treatment channel 124.

The device 120 extends between first and second ends where the device may be anchored distal to the renal arteries 8a, 8b and a second location downstream of an aneurysm. The blood flow channel 122 is operable to direct or channel blood through the device. The treatment channel 124 comprises a plurality of lumens or apertures 126 to drain blood from an internal area 128 of an aneurysm. The treatment channel 124 is further operable to deliver a drug or substance to an aneurysm for treatment. The aneurysm depicted in FIG. 8 comprises a complex, irregular nature including an intraluminal thrombus 130 and a saccule with thrombus 134. In the embodiment of FIG. 8, the device 120 comprises mechanical basket members 136, 138 at each end of the device. The baskets are selectively and mechanically expandable to contact an interior of the aortic wall and direct blood flow as shown. The device is operable to isolate blood flow from the aneurysmal wall that it would otherwise contact. The internal volume of the aneurysm may thus be drained and treated with a liquid drug or stabilizing substance 132. Although FIGS. 7 and 8 provide expandable balloons and mechanical baskets, it should be recognized that these concepts are not necessarily mutually exclusive, and, in some embodiments, the device comprises a combination of balloons and expandable mechanical baskets. The expandable baskets may be self-expandable structures with sufficient outward radial force to anchor the respective ends of the device. They may be expanded by a push-pull action of inner and outer members as has been previously described. They may represent stent like structures which anchor the respective ends of the device. They may be partially covered with an elastomer, and in this instance, the cephalic placed basket may be expanded at least partially by the patient's blood pressure as the blood flows into it.

Importantly, an aneurysm stabilizing substance may comprise substances that act in one or more pathways to stabilize the wall of the aneurysm internally as discussed previously. Also, other substances that do not act directly upon the components of the aortic wall may be utilized in the configurations of FIGS. 6, 7, and 8 and may include substances such as polymers, acrylics, glues, auto-polymerizing resins, thrombin, hydrogels, coils and other physical fillers, filler substances amongst other substances that may be injected through a catheter into the excluded aortic sac, but solidify into a cast like shape within the excluded aneurysmal sac that is excluded by the flow through component. The substances may not be chemically active at all, but only fill the space in the aneurysmal sac not occupied by the flow through component. However, the filler substance or substances may be combined with one or more of the active agents previously discussed so to fill the excluded aneurysmal sac and protect the wall from systolic and diastolic pressures and provide active substances to repair the internal damage of the aortic wall.

The method comprises placing the device 100 within an aorta, expanding the blood flow channel 111, inflating the balloons 104, 106, flushing or irrigating the blood in the excluded aneurysmal sac via the treatment channel 113, injecting one or more of a fluid aneurysm stabilizing substance and a filler substance through the treatment channel 113 and into the excluded aneurysmal sac, waiting a period of time for the filler substance to solidify, and then removing the device.

An alternate method comprises placing the device 100 within an aorta, expanding the blood flow channel 111, inflating the balloons 104, 106, flushing or irrigating the blood in the excluded aneurysmal sac via the treatment channel 113, injecting a fluid aneurysm stabilizing substance through the treatment channel 113 and into the excluded aneurysm sac, waiting a period of time and leaving the scaffold in place. Preferably, the filler substance should not adhere to the catheter or membrane on the outer surface of the flow through scaffold. Hence, catheters to deliver the filler substance and membranes about the scaffold to contain the filler substances within the excluded aortic sac may compromise materials that do not adhere to the filler substances. This would allow the insertion of the filler substances and the withdrawal of the scaffold and membrane after the filler substances have consolidated and solidified into a cast. Importantly, the filler substance may comprise other compounds listed herein which stabilize the wall of the aorta through one or more pathways. Hence, in this latter configuration, the filler substance will fill the weakened aortic aneurysmal sac and serve as a reservoir of sorts for the aneurysmal stabilizing substances to leach into the aneurysmal wall over time from the filler substance cast.

Often the complex aneurysm may extend into one or both common iliac arteries. This may cause difficulty with applying or delivering the aneurysm stabilizing substance to the walls of these dilated arteries. Smaller versions of many of these embodiments may be utilized to treat these areas separately from the main aortic aneurysm.

For complex aneurysm, a device specific to a particular patient may also be employed. In this embodiment, high resolution images or data collected in the workup may be utilized with computer aided design to produce a delivery device that is shaped exactly like the aneurysm in question. This expansive device, which may be similar to FIGS. 1-5, may be of same dimensions as the aneurysm so that when deployed in the correct orientation, it fits snugly against the aneurysm wall, even into saccules and angulations.

Additionally, other embodiments may consist of devices for injecting the aneurysm stabilizing substance into the periaortic tissues from a trans lumbar approach or from a vascular approach.

Another embodiment may consist of a compliant drug coated balloon in the mid portion and more non-compliant drug coated or non-drug coated balloons at each end. This may allow firm attachment and anchoring of the device while utilizing a compliant balloon to deliver the substance with less outward pressure.

In any of the embodiments described herein, a catheter like device comprising an aneurysm stabilizing substance may be inserted percutaneously and directed to the aneurysmal dilatation area, the delivery component expanded to contact the wall of the aneurysm, the expanded delivery component left expanded and contacting the aneurysmal wall for a period of time to deliver the aneurysm stabilizing substance to the aneurysmal endothelium where it is transferred from the delivery component to the endothelium and the delivery component collapsed and the entire device removed from the body.

While the discussion herein utilizes abdominal aortic aneurysms as an example, the technology, devices, embodiments, and methods are also applicable to aneurysms in the thoracic aorta and other vessels. Moreover, the technology, embodiments, devices, and methods described herein may be utilized to deliver substances or medicaments to non-aneurysm affected vessels or to otherwise treat in some manner vascular, malignant, or other disorders. For example, the devices and methods may be utilized to deliver substances to the arterial wall after balloon angioplasty, atherectomy, or other intervention similar to drug coated balloons. The methods and devices also may be utilized to deliver medicaments or substances to valvular structures, intracranial aneurysms, organs with tumors, to stabilize or treat areas of vulnerable plaque, to treat areas of restenosis or prevent restenosis, to lyse thrombus on the vessel wall, amongst other uses.

Multiple mechanisms/biochemical pathways are involved in the formation and progression of aneurysms, and effective treatment of aneurysms requires targeting as many of these mechanisms or pathways simultaneously, to prevent degradation and ensure vascular tissue matrix and cellular regeneration. Examples of the mechanisms/pathways promoting or contributing to the formation and progression of aortic aneurysm are discussed below. Aneurysmal stabilizing substances include substances that target one or more of these mechanisms/pathways.

Elastin, collagen and hyaluronan are components of tissue matrix that are important for aortal integrity. For effective aneurysm treatment, degradation of these components needs to be inhibited, and/or their production enhanced. For example, several steps are required for elastin production and deposition, each of which may be disrupted during formation and progression of aneurysm but most commonly the following steps are disrupted: cross-linking of elastin by lysyl oxidase (LOX/LOXL), directed assembly of cross-linked elastin into microfibrils, and growth and maturation of elastin fibers including proper deposition of microfibrils throughout tissue matrix. For effective aneurysm treatment, the disruption of elastin production steps needs to be inhibited. Accordingly, aneurysmal stabilizing substances include therapeutic agents inhibiting elastin, collagen and/or hyaluronan degradation and/or restoring or improving their production and deposition. Such agents include, but are not limited to: tannins, polyphenols and related agents, including but not limited to epigallocatechin gallate (EGCG), white/green tea extract (high in EGCG), pentagalloyl glucose (PGG), tannic acid, grape seed extract, ruscogenins, *Ruscus aculeatus* extract (high in ruscogenins), diosmin, hesperidin, hederagenin, escin, *Aesculus hippocastanum* extract (high in escin), pycnogenol, etc.; other elastase, collagenase or hyaluronidase inhibitors, including but not limited to doxycycline hyclate; inhibitors of cysteine proteinases (particularly inhibitors of cathepsins and calpain); inhibitors of serine proteinases, including but not limited to camostat; and enhancers of LOX/LOXL production and/or activity, including but not limited to dill seed extract.

Regardless of how aneurysm formation starts, the aneurysm is typically associated with an inflammatory process that can damage arterial wall via several mechanisms, including increase in production of free radicals, induction of migration of a variety of immune cells into aortic wall, and increase in the production of inflammation signaling molecules (interleukins, prostaglandins, leukotrienes, thromboxanes and others). These inflammatory mechanisms are interrelated and all lead to activation of matrix metalloproteinases and other matrix degrading enzymes (particularly elastase, collagenase and hyaluronidase, the enzymes that degrade elastin, collagen and hyaluronan correspondingly), and suppress production of endogenous protease inhibitors. For effective aneurysm treatment, the inflammatory mechanisms need to be inhibited. Accordingly, aneurysmal stabilizing substances include therapeutic agents inhibiting/modulating inflammation in the aortic wall. Such agents include but are not limited to: lymphocyte function suppressors, including but not limited to cyclosporine; luekotriene receptor inhibitors, including but not limited to montelukast, zafirlukast; nf-kb inhibitors; prostaglandin/leukotriene antagonists and synthesis inhibitors/modulators, including but not limited to COX, COX-2 enzyme inhibitors; omega-3 fatty acids, including but not limited to DHA and EPA; immunomodulatory/anti-inflammatory cannabinoids, including but not limited to: cannabidiol; sphingosine-1-phosphate receptor modulators, including but not limited to fingolimod; agents that reduce free radical damage, such as antioxidants, free radical scavengers, oxidative stress modulators, including but not limited to superoxide dismutase, catalase, glutathione peroxidase, tocopherols, tocotrienols, glutathione, etc.; statins, including but not limited to atorvastatin, fluvastatin, lovastatin, pravastatin, rosuvastatin, simvastatin, pitavastatin, etc.; and boosters of cellular NAD+ levels, including but not limited to nicotinamide riboside (NR) and nicotinamide mononucleotide (NMN).

Apoptosis (programmed cell death) is often a consequence of other mechanisms involved in the development of aneurysm. However, it can also contribute to aneurysm pathology. Inhibiting apoptosis may produce therapeutic benefits, especially when there is a high risk of rupture. Accordingly, aneurysmal stabilizing substances include therapeutic agents for inhibiting apoptosis of cells in the aortic wall. Such agents include but are not limited to: inhibitors of cysteine-aspartic proteases (caspases), including but not limited to VX-765.

An aneurysmal stabilizing substance may also be an agent useful in gene therapy. Such agents may function to promote overexpression of certain proteins. For example, such agents may promote overexpression of tissue inhibitors of matrix metalloproteinases (TIMPs) (which inhibit elastase and collagenase), elastin and tropoelastin, transforming growth factor-beta1, LOX/LOXL (this will need to be short-term and/or inducible as long-term LOX/LOXL overexpression may have negative side effects), and enzymes that reduce oxidative stress, including but not limited to, superoxide dismutase, catalase, glutathione peroxidase. Alternatively, such agents may suppress expression of certain proteins. For example, such agents may comprise suppressor microRNAs which suppress expression of elastase, collagenase, hyaluronidase, cysteine proteinases (particularly cathepsins and calpain), nf-kb, pro-inflammatory cytokines or cysteine-aspartic proteases (caspases).

A variety of targeted gene therapy vehicles may be used, such as adjusted adeno virus (AAV), lentivirus, plasmid based vectors and others. Gene therapy vectors, such as AAAV particles, can be delivered to the affected tissue via delivery device described herein without significantly affecting other tissues. The duration of overexpression can be calibrated by selecting appropriate vectors, using inducible promoters and other means. Gene therapy may involve coordinated overexpression of a variety of genes that can, acting in concert, halt or reverse the development of aneurysm.

In some embodiments, the present invention includes a composition useful in the treatment of aneurysms comprising an effective amount of one or more aneurysmal stabilizing substances. Some compositions may contain an effective amount of at least two, at least three, at least four, or at least five, aneurysmal stabilizing substances. In some compositions, a combination of aneurysmal stabilizing substances that simultaneously target more than one mechanisms/pathways discussed above may be used. Some compositions may contain phenolic and non-phenolic aneurysmal stabilizing substances.

For the avoidance of doubt, it is clarified that the delivery device described herein is agnostic to the specific substance to be delivered and may be used to deliver any substances. The substance to be delivered is not limited to an aneurysm stabilizing substance and may comprise anti-inflammatory properties, antirestenotic properties, anticoagulant or antiplatelet properties, antibiotic properties, gene therapy, chemotherapy, anti-malignant properties or any substance that may directly or indirectly affect the vessel or organ to which it is applied amongst other uses.

Additionally, many of the changes that cause or contribute to aneurysmal formation and enlargement are also responsible for age related changes in the skin, and the pathways that contribute to aneurysm formation and enlargement are the same or similar pathways that occur in cutaneous and subcutaneous tissue that cause sagging, wrinkled, and unelastic skin changes. Therefore, the compositions comprising aneurysmal stabilizing substances described herein are also useful in treating age related and other changes in the skin.

While the present invention has been illustrated by description of preferred embodiments and while the illustrative versions have been described in considerable detail, it is not the intention of the inventors to restrict or in any way limit the scope of the appended claims to such detail. Additional advantages and modifications will readily appear to those skilled in the art upon reading this detailed description. Therefore, the invention, in its broader aspects, is not limited to these specific details, respective apparatus and methods, and illustrative examples shown and described. Accordingly, departures may be made from such details without departing from the spirit or scope of the inventor's general inventive concepts.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An intravascular device for treating an aneurysm and delivering a substance to the aneurysm, the device comprising:
   an insertion catheter;
   a stent comprising a distal end and a proximal end and a length extending between the proximal end and the distal end, and wherein the stent is operable to be inserted within an artery;

wherein at least one of the distal end and the proximal end of the stent is permanently attached to the distal end of the insertion catheter by substantially rigid guide wires;

the stent comprising an inlet operable to receive blood flow at the distal end and an outlet operable to allow the egress of blood flow at the proximal end;

wherein the stent comprises a continuous expandable membrane provided between the distal end and the proximal end that is operable to expand and make continuous contact with an interior portion of an artery from the distal end to the proximal end to treat an aneurysm in the artery and secure the stent relative to the artery, the expandable membrane being operable to deliver a drug or substance to an aneurysm external to the stent; and wherein the distal end of the stent is permanently connected to a distal end of an inner member of the insertion catheter by a plurality of substantially rigid guide wires and the proximal end of the stent is permanently connected to an outer member of the insertion catheter by a second plurality of substantially rigid guide wires.

2. The intravascular device of claim 1, wherein the expandable membrane comprises at least one aneurysmal stabilizing substance that is selected from the group consisting of:

(a) therapeutic agents inhibiting elastin, collagen and/or hyaluronan degradation and/or restoring or improving their production and deposition selected from the group consisting of tannins, polyphenols and related agents, elastase inhibitors, collagenase inhibitors, hyaluronidase inhibitors, inhibitors of cysteine proteinases, inhibitors of cathepsins, inhibitors of calpain, inhibitors of serine proteinases and enhancers of LOX/LOXL production and/or activity;

(b) therapeutic agents inhibiting/modulating inflammation in the aortic wall selected from the group consisting of lymphocyte function suppressors, luekotriene receptor inhibitors, nf-kb inhibitors, prostaglandin/leukotriene antagonists and synthesis inhibitors/modulators, immunomodulatory/anti-inflammatory cannabinoids, sphingosine-1-phosphate receptor modulators and agents that reduce free radical damage selected from the group consisting of antioxidants, free radical scavengers, oxidative stress modulators, statins and boosters of cellular NAD+ levels; and (c) therapeutic agents inhibiting apoptosis of cells in the aortic wall selected from the group consisting of inhibitors of caspases.

3. The intravascular device of claim 1, wherein the stent comprises a single inlet operable to receive blood flow at the distal end and at least one outlet operable to allow the egress of blood flow at the proximal end, wherein the inlet of the stent comprises an area that is greater than the area of the at least one outlet of the stent, and wherein the expandable membrane is operable to be expanded at least in part by a force provided by a flow of blood entering the inlet of the stent.

4. The intravascular device of claim 1, wherein the insertion catheter comprises an inner member and an outer member.

5. The intravascular device of claim 4, wherein the inner member and the outer member are translatable relative to one another and wherein a translation of the inner member relative to the outer member is operable to expand and to collapse the stent.

6. The intravascular device of claim 4, wherein the stent is secured to the inner member at the distal end of the stent and secured to the outer member at the proximal end of the stent.

7. The intravascular device of claim 1, wherein a minimal outward radial force generated by the intravascular device is less than 10% of an outward radial force generated by the patient's own blood pressure.

8. The intravascular device of claim 1, wherein at least a portion of the distal end and at least a portion of the proximal end of the stent are expandable between a first diameter and a second diameter.

9. An intravascular device for treating an aneurysm and delivering a substance to the aneurysm, the device comprising:

an insertion catheter;

a stent comprising a distal end and a proximal end and a length extending between the proximal end and the distal end, and wherein the stent is operable to be inserted within an artery;

wherein at least one of the distal end and the proximal end of the stent is permanently attached to the distal end of the insertion catheter by substantially rigid guide wires;

the stent comprising an inlet operable to receive blood flow at the distal end and an outlet operable to allow the egress of blood flow at the proximal end;

wherein the stent comprises a continuous expandable membrane provided between the distal end and the proximal end that is operable to expand and make continuous contact with an interior portion of an artery from the distal end to the proximal end to treat an aneurysm in the artery and secure the stent relative to the artery, the expandable membrane being operable to deliver a drug or substance to an aneurysm external to the stent;

wherein the insertion catheter comprises an inner member and an outer member and the inner member and the outer member are translatable relative to one another and wherein a translation of the inner member relative to the outer member is operable to expand and to collapse the stent.

\* \* \* \* \*